United States Patent [19]

Bernardi et al.

[11] Patent Number: 4,558,049

[45] Date of Patent: Dec. 10, 1985

[54] ANTIPSYCOTIC BENZOXAZINES

[75] Inventors: Luigi Bernardi; Ettore Lazzari, both of Milan; Maria L. Malnati, Nese; Giuseppe Mazzini, Milan; Lorenzo Pegrassi, Milan; Alessandro Rossi, Milan, all of Italy

[73] Assignee: Farmitalia Carlo Erba S.p.A., Milan, Italy

[21] Appl. No.: 493,618

[22] Filed: May 11, 1983

[30] Foreign Application Priority Data

Nov. 24, 1982 [GB] United Kingdom ............... 8233533

[51] Int. Cl.[4] .................. A61K 31/535; C07D 498/10
[52] U.S. Cl. .................................. 514/234; 514/237; 514/239; 544/71
[58] Field of Search .............. 544/71; 424/248.56, 424/248.57; 514/234, 237, 239

[56] References Cited

U.S. PATENT DOCUMENTS 4,349,549 9/1982 Roszkowski et al. ......... 544/71 X

FOREIGN PATENT DOCUMENTS 70171 1/1983 European Pat. Off. .

Primary Examiner—Richard L. Raymond
Attorney, Agent, or Firm—Oblon, Fisher, Spivak, McClelland & Maier

[57] ABSTRACT

There are provided compounds of formula 1:

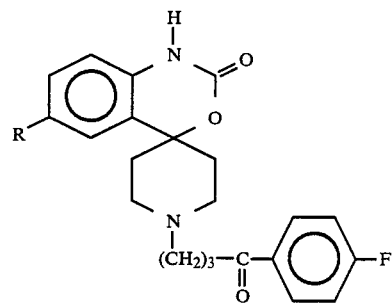

wherein R=halogen atom or CN, $NH_2$ and $NO_2$ group, and pharmaceutically acceptable salts thereof.

The compounds are antipsycotic agents.

3 Claims, No Drawings

ANTIPSYCOTIC BENZOXAZINES

BACKGROUND OF THE INVENTION a. Field of the Invention

The invention herein relates to a class of benzoxazines which have valuable pharmacological activities on the Central Nervous System and are useful in treating psychic disorders, especially schizophrenic syndromes.

b. Description of the Prior Art

The literature describes other compounds having similar structures, but different activity from that of the compounds of this invention. For example U.S. Pat. No. 4,349,549 issued on Sept. 14, 1982 disclosed spiro-(piperidin-oxobenzoxazines) having antihypertensive activity.

SUMMARY OF THE INVENTION

This invention provides 1'-(3-benzoylpropyl)spiro-(3,1-benzoxazine-4(2H)4'-piperidin)-2-ones and their pharma acceptable salts, of formula

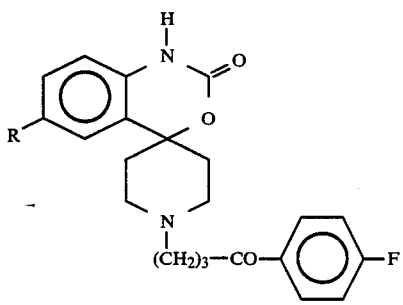

wherein R represents a halogen atom or a cyano, amino, or nitro group.

The compounds of formula I are antipsycotics.

DETAILED DESCRIPTION OF THE INVENTION

"Pharmaceutically acceptable salts" refers to the salts which retain the biological effectiveness and properties of the free bases and which are not biologically or otherwise undesiderable. Suitable acids for the preparation of the salts include hydrochloric, hydrobromic, sulphuric, acetic, propionic, lactic, citric, tartaric, methanesulphonic acids and the like.

Preferred halogens which R may represent, include chloro, bromo and fluoro.

DESCRIPTION OF THE PREFERRED EMBODIMENTS

Particularly preferred compounds according to the present invention are:

1'-[3-(4-Fluorobenzoyl)-propyl]spiro-(3,1-benzoxazine-6-bromo-4(2H)4'piperidin)-2-one.

1'-[3-(4-Fluorobenzoyl)propyl]spiro-(3,1-benzoxazine-6-nitro-4(2H)4'-piperidin)-2-one.

1'[3-(4-Fluorobenzoyl)propyl]spiro-(3,1-benzoxazine-6-fluoro-4(2H)4'-piperidin)-2-one.

1'[3-(4-Fluorobenzoyl)propyl]spiro-(3,1-benzoxazine-6-cyano-4(2H)4'-piperidine)2-one.

All the compounds and salts of the present invention present interesting pharmacological activities on the Central Nervous System. More particularly the present compounds display significant activity as antipsycotic agents with a very low toxicity and incidence of side effects in comparison with haloperidol (II)

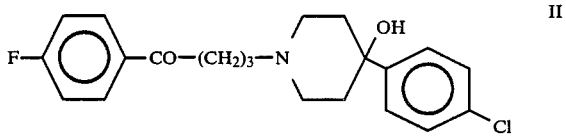

which is a widely used drug in the therapy of psychic disorders, especially of schizophrenic syndromes.

The compounds and salts of the invention proved very active as antagonists to apomorphine-induced climbing behaviour in mice, i.e., as central dopaminergic antagonists, following the technique of Protais P. et al. (Psychopharmacology, 50, 1 (1976).

The classical neuroleptics may be even more active in the above-mentioned experimental model, but are exceedingly active in disrupting behavioural performance. On the contrary, the compounds and salts of this invention gave results which were less active or inactive in a series of tests which comprise the undesired side-effects on neuromuscular coordination in the rat by the rotarod test (Dunham, M. W. et al, J.Am.Pharm.Ass. 46, 208 (1957)), the interference wth conditioned Avoidance Response in the rat (Gupta, B. D. et al, Psychopharmacologia, 14, 95 (1969)), the potential induction of catalepsy in rats (catalepsy is generally defined as the condition in which an animal will allow itself to be placed in unusual body positions which are maintained for extended time intervals, e.g., Rech, R. H. et al, "An Introduction to Psychopharmacology" Raven Press, N.Y., 1971, and "The Potential antagonism to rational behaviour produced by dopaminergic agents in rats with 6-OHDA induced unilateral lesions of the dopaminergic nigrostriatal pathway", (Ungerstedt, U. et al, Brain Res. 14, 461, 1969).

The compounds and salts of the invention were also tested following Irwin S. "Technique in mice" (Psychopharmacologia 13, 322 (1968)) and have been shown to interfere weakly with spontaneous activity and body temperature, and to have very low toxicities. A summary of the main pharmacological features of the compounds and salts of the present invention versus haloperidol are reported to the Table below.

TABLE

| Tests | Compound of Example 1 | Compound of Example 3 | Haloperidol |
| --- | --- | --- | --- |
| Apomorphine antagonism in mice ($ED_{50}$, mg/kg p.o.) | 1.7 | 2.7 | 0.2 |
| Reduction of spontaneous activity and body temperature in mice (min. active does, mg/kg p.o.) | 12.5 100 | 15 110 | 0.78 3.12 |
| ~$LD_{50}$ in mice (mg/kg p.o.) | >800 | >800 | 75 |
| Min. active doses (rat, mg/kg p.o.) in: | | | |

| Tests | Compound of Example 1 | Compound of Example 3 | Haloperidol |
| --- | --- | --- | --- |
| Rotarod test | >50 | 50 | 0.5 |
| C.A.R. test | 25 | 20 | 0.5 |
| Turning-behaviour | >20 | >15 | 0.5 |
| Catalepsy induction | >200 | 200 | 0.5 |

As this pharmacological profile shows, the compounds of the invention are more selective antipsychotic agents than haloperidol. They are in fact potent central dopamine-antagonists with far lower incidence of disrupting effects on behavioural performance and with very low toxicities.

The involvement of dopamine in psychotic states is strongly suggested by several clinical observations based not only on the fact that all known neuroleptic drugs block dopamine receptors whereas even structurally related compounds devoid of such an effect do not show therapeutic activity, but also on the finding that dopamine agonists or dopamine-releasing agents can produce worsening of pre-existing psychosis in patients with active schizophrenic illness. The block of dopamine receptor systems may be more or less specific and can occurr in different districts of the organism. A widespread blockage of dopamine receptors usually results in hinge behavioural impairment, as happens under treatment with the typical so-called neuroleptics. Nearly all of the currently available neuroleptic agents produce in fact a variety of neurological disorders in both laboratory animals and patients. The compounds and salts of this invention show a more selective antipsychotic profile, being very potent central dopamine antagonists with very weak or no influence on muscular tone, neuromuscular coordination, behavioural performance and arterial pressure, as shown by the data of the Table, and therefore are expected to be used with advantage in the therapy of psychotic disorders.

Accordingly, two other aspect of the invention relate to pharmaceutical compositions containing the compounds of formula I, and to methods for treating psycotic disorders using said compounds and said composition. Compounds of formula I and their salts described herein may be administered by parenteral or oral route, preferably by oral route.

Depending on administration route, the compositions may be in the form of solid, semi-solid or liquid dosage form, such as, for example, tablets, pills, capsules, powders, liquids, suspension or the like.

The composition will include a conventional pharmaceutical carrier or excipient and an active compound of formula I or the pharmaceutically acceptable salt thereof and, in addition, may include other medicinal agents, pharmaceutical agents, carriers, adjuvants, etc. The dosage of the present drugs varies in accordance with the sex, age, condition or medical record of the patient, as well as according to the route or purpose of the administration. In general, the drugs may be administered as single doses or as divided doses so as to provide, say, about 0.01–20 mg/kg body weight per day of effective ingredient, preferably about 0.03–11 mg/kg body weight.

The pharmaceutical compositions containing the compounds of the invention are prepared according to conventional methods with the usual ingredients. Thus, for oral administration, the pharmaceutical compositions containing the compounds of the invention are preferably tablets, pills or capsules which contain the active substance together with diluents, such as, for example, lactose, dextrose, sucrose, mannitol, sorbitol, sucrose, cellulose; lubricants, for instance, silica, talc, stearic acid, magnesium or calcium stearate and/or polyethylene glycols; or they may also contain binders, such as, for example, starches, gelatine, methylcellulose, gum-arabic, tragacanth, polyvinylpyrrolidone; disintegrating agents, such as, for instance, starches, alginic acid, alginates; effervescing mixtures; dyestuffs; sweeteners; wetting agents, such as, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

Also the other pharmaceutical formulations containing the compounds of the invention may be prepared by known methods and they can be, for example, syrup or drops for the oral administration, sterile solutions for injection, or suppositories.

GENERAL METHOD OF PREPARATION

The compounds of formula I are prepared by means of alkylation of spiro(3,1-benzoxazine-4(2H)4'-piperidin)-2-ones of formula III

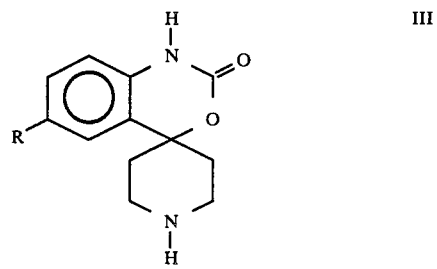

with compounds of formula IV or V

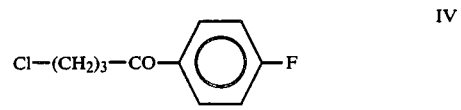

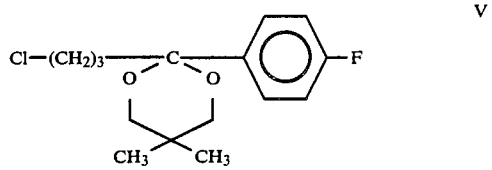

wherein R has the meanings given above. This reaction is generally carried out in the presence of potassium iodide and of an organic or inorganic base, such as triethylamine, potassium carbonate or sodium bicarbonate in a suitable solvent such as an alcohol having up to 6 carbon atoms, toluene, benzene, acetonitrile, dimethylformamide and tetrahydrofuran at a temperature in the range from about 50° to about 160° C. Preferably the alkylation reaction is carried out by reacting the two substances at 100° C. in the presence of potassium iodide and anhydrous potassium carbonate and using dimethylformamide as solvent and the protected compound V as alkylating reagent. The reaction mixture is treated with hydrochloric acid in methanol to give the 1'-benzoylpropylspiro-)3,1-benzoxazine-4(2H)4'-piperidin)-2-ones of formula I. The compounds of formual III, which are the main intermediates, are prepared as shown in scheme A below.

Scheme A

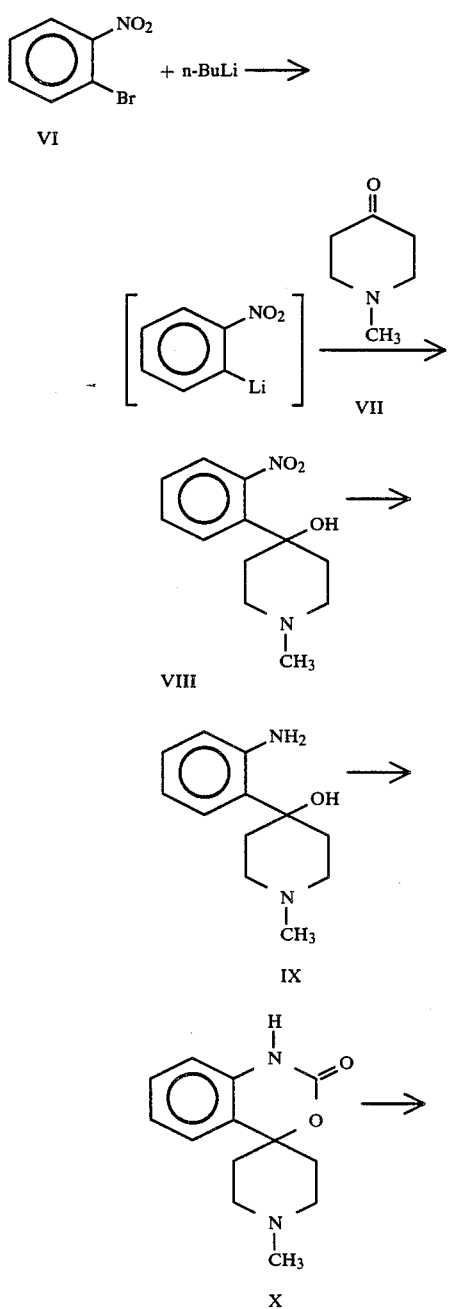

-continued
Scheme A

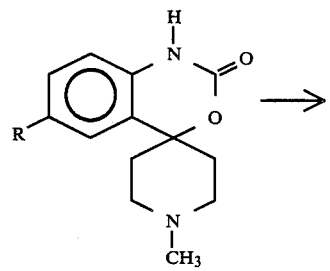

XI

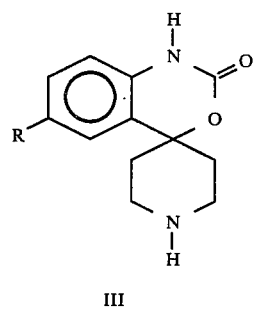

III

A 2-bromonitrobenzene VI is metalated at about −100° C. by halogen-metal exchange with n-Buli, and then reacted with 1-methyl-4-piperidone VII to give the nitrocarbinol VIII. The nitro group is then catalytically reduced to the amino carbinol IX which is cyclized to compound X by reacting with phosgene or carbonyldiimidazole.

Compounds of formula X are transformed into compounds of formula XI wherein R represents halogen atom, nitro, amino or cyano group by reaction known per se, e.g. aromatic halogenation, nitration, nitration and reduction, diazotisation and diazo replacement respectively, as described in the Examples below.

The intermediate compound of formula III is obtained from XI by means of dealkylation via von Braun reaction.

The following examples illustrate the invention but are not intended to limit it thereto. Temperatures are in °C.

EXAMPLE 1

1'-[3-(4-Fluorobenzoyl)propyl]spiro-(3,1-benzoxazine-6-bromo-4(2H)4'-piperidin)-2-one Step one: The Intermediate 1-methyl-4-(2-nitrophenyl)-4-hydroxypiperidine To a solution of 19.3 g of 2-bromonitrobenzene in 480 ml of anhydrous tetrahydrofuran cooled to −100° C., 79 ml of 1,6M solution of n-Buli in hexane are dropped under N₂. After two hours 10.9 g of 1-methyl-4-piperidone are added and the resulting mixture is stirred eight hours at −100° C. Then 1N hydrochloric acid is added at 0° C. to acidify to pH 2 and the solution is extracted with hexane. The aqueous phase is brought to pH 10 and extracted with ethyl ether. Evaporation of the extracts gives 8.95 g of 1-methyl-4(2-nitrophenyl)-4-hydroxypiperidine, m.p. 166°–167°.

Step two: The intermediate 1-methyl-4-(2-aminophenyl)-4-hydroxipiperidine

A mixture of 25 g of the above prepared compund and 2 g of 10% Pd/C in 1000 ml of ethanol is hydrogenated at 20° C. and at atmospheric pressure. The reaction mixture is then filtered and evaporated to dryness yielding 20.5 g of 1-methyl-4(2-aminophenyl)-4-hydroxypiperidine, m.p. 135°–136° from diisopropyl ether.

Step three: The intermediate 1'-methylspiro-(3,1-benzoxazine-4(2H)4'-piperidin)-2-one To a well stirred solution of 13 g of 1-methyl-4-(2-aminophenyl)-4-hydroxypiperidine in 400 ml of anhydrous tetrahydrofuran a solution of 12.74 g of carbonyldiimidazole in 120 ml of tetrahydrofuran is added. After stirring twenty hours the solution is concentrated to a small volume and 200 ml of chloroform are added. The solution is washed four times with water, dried over sodium sulphate and evaporated to yield 14.52 g of 1'-methylspiro-(3,1-benzoxazine-4(2H)4'piperidin)-2-one, m.p. 156°–157° after recrystallization from ethyl acetate.

Step four: The intermediate 1'-methylspiro-(3,1-benzoxazine-6-bromo-4(2H)4'piperidin)-2-one A solution of 22.3 g of bromine in 75 ml of acetic acid is dropped at 15° into a solution of 16.2 g of 1'-methyl-spiro-(3,1-benzoxazine-4(2H)4'piperidin)-2-one and 6.3 g of anhydrous sodium acetate in 280 ml of acetic acid. The mixture is stirred overnight at room temperature and filtered. The reddish solid is dissolved in methylene chloride and washed with a 15% aqueous solution of sodium bisulphite. The organic phase is dried over magnesium sulphate and evaporated to give 16.45 g of 1'-methylspiro-(3,1-benzoxazine-6-bromo-4(2H)4'-piperidin)-2-one, m.p. 210°–212°.

Step five: The intermediate 1'-cyanospiro-(3,1-benzoxazine-6-bromo-4(2H)4'-piperidin)-2-one A solution of 15.5 g of 1'-methylspiro-(3,1-benzoxazine-6-bromo-4(2H)4'-piperidin)-2-one in 150 ml of chloroform is slowly added to a stirred boiling solution of 7.91 g of cyanogen bromide in 160 ml of chloroform under nitrogen and the resulting solution is refluxed ten hours. The unreacted starting material is extracted with 0.5N hydrochloric acid. The chloroform solution is then washed with water, dried over sodium sulphate and evaporated to give 12.75 g of 1'-cyanospiro-(3,1-benzoxazine-6-bromo4(2H)4'-piperidin)-2-one, m.p. 275°–276° from acetonitrile.

Step six: The intermediate spiro-(3,1-benzoxazine-6-bromo-4(2H)4'-piperidin)-2-one A solution of 12 g of 1'-cyanospiro-(3,1-benzoxazine-6-bromo-4(2H)4'-piperidin)-2-one. in 180 ml of dimethylformamide, 80 ml of water and 120 ml of 37% hydrochloric acid is refluxed three hours. The cooled mixture, diluted with 500 ml of water, is basified with a concentrated solution of sodium hydroxide and extracted with n-butanol. By vacuum concentration of the butanol 10.8 g of spiro-(3,1-benzoxazine-6-bromo-4(2H)4'-piperidin)-2-one are obtained, m.p. 253°–255° after recrystalization from acetonitrile.

Step seven: The title compound

A mixture of 0.6 g of the above described spiro-(3,1-benzoxazine-6-bromo4(2H)4'-piperidin)-2-one, 0.36 g of potassium iodide, 0.6 g of anhydrous potassium carbonate and 0.53 g of 2-(3-chloropropyl)-2-(4-fluorophenyl)-5,5-dimethyl-1,3-dioxane in 6 ml of dimethyl-formamide is heated at 100°. After four hours, the inorganic salts are filtered off and the solvent is removed in vacuo.

The crude acetal thus obtained is then hydrolyzed by stirring two hours at room temperature in 15 ml of methanol and 7.5 ml of 2.5N hydrochloric acid. This solution is concentrated, basified with 20% aqueous sodium hydroxide and extracted with chloroform. The extracts are evaporated to give 0.57 g of 1'-[3-(4-fluorobenzoyl)propyl]spiro-3,1-benzoxazine-6-bromo-4(2H)4'-piperidin)-2-one, m.p. 206°–208°, from ethyl acetate.

EXAMPLE 2

1'[3-(4-fluorobenzoyl)propyl]spiro-(3,1-benzoxazine-6-chloro-4(2H)4'-piperidin)-2-one

Step one: The intermediate 1'-methylspiro-(3,1-benzoxazine-6-chloro-4(2H)4'-piperidin)-2-one A solution of 5.6 ml of sulphuryl chloride in 55 ml of dichloromethane is added dropwise to a solution of 8 g of 1'-methylspiro-(3,1-benzoxazine-4(2H)4'-piperidin)-2-one (Example 1) in 80 ml of dichloromethane at 0°. The resulting mixture, after stirring two days at room temperature, is filtered off yielding 9.8 g of 1'-methyl-spiro-(3,1-benzoxazine-6-chloro-4(2H)4'-piperidin)-2-one, hydrochloride. The free base has m.p. 209°–212°.

Step two: The intermediate 1'-cyanospiro-(3,1-benzoxazine-6-chloro-4(2H)4'-piperidin)-2-one Starting from 6 g of the above prepared 6-chloroderivative and 3.9 g of cyanogen bromide according to the previously described procedure (see Example 1—step five) 4.7 g of 1'-cyanospiro-(3,1-benzoxazine-6-chloro4(2H)4'-piperidin)-2-one, m.p. 250°, are obtained.

Step three: The intermediate spiro-(3,1-benzoxazine-6-chloro-4(2H)-4'-piperidin)-2-one 4.5 g of the 1'-cyanospiro derivative above described are hydrolyzed according to the usual procedure giving 3.3 g of spiro-(3,1-benzoxazine-6-chloro-4'-piperidin)-2-one, m.p. 230°–232°.

Step four: The title compound

Starting from 2.6 g of spiro-(3,1-benzoxazine-6-chloro-4(2H)4'-piperidin)-2-one, 1.8 g of potassium iodide, 3.1 g of anhydrous potassium carbonate and 2.4 g of 2-(3-chloropropyl)-2-(4-fluorophenyl)-5,5-dimethyl-1,3-dioxane in 30 ml of dimethylformamide, 2.6 g of 1'-[3-(4-fluorobenzoyl)propyl]spiro-(3,1-benzoxazine-6-chloro-4(2H)4'-piperidin)-2-one, m.p. 186°–188° are obtained according to the previously described procedure.

EXAMPLE 3

1'-[3-(4-fluorobenzoyl)propyl]spiro-(3,1-benzoxazine-6-nitro-4(2H)4'-piperidin)-2-one

Step one: The intermediate 1'-methylspiro-(3,1-benzoxazine-6-nitro-4(2H)4'piperidin)-2-one 19.2 g of 1'-methylspiro-(3,1-benzoxazine-4(2H)4'-piperidin)-2-one (Example 1) are dissolved in 80 ml of concentrated sulphuric acid and 6.2 ml of 65% nitric acid is added at −15° C. After stirring one hour the resulting mixture is poured into 300 g of ice-water and then filtered off giving the sulphate of 1'-methylspiro-(3,1-benzoxazine-6-nitro-4(2H)4'-piperidin)-2-one from which 21.2 g of free base, m.p. 258°–261°, are obtained after basic treatment.

Step two: The intermediate 1'-cyanospiro-(3,1-benzoxazine-6-nitro-4(2H)4'-piperidin)-2-one A solution of 10 g of the above prepared 6-nitro derivative in 80 ml of dimethylformamide and 120 ml of chloroform is added to a boiling solution of 8.3 g of cyanogen bromide in 100 ml of chloroform and the mixture is refluxed eight hours. 200 ml of chloroform are added and the solution is washed with 10% aqueous solution of tartatic acid, with a saturated solution of sodium bicarbonate and with a saturated solution of sodium chloride. Evaporation of the chloroform gives 7.1 g of 1'-cyanospiro-(3,1-benzoxazine-6-nitro-4(2H)4'-piperidin)-2-one, m.p. 270° dec.

Step three: The intermediate spiro-(3,1-benzoxazine-6-nitro-4(2H)4'-piperidin)-2-one A solution of 7.05 g of 1'-cyanospiro-(3,1-benzoxazine-6-nitro-4(2H)4'-piperidin)-2-one in 125 ml of dimethylformamide, 58 ml of water and 81.5 ml of concentrated hydrochloric acid is refluxed one hour. The mixture is cooled and filtered off giving 5.5 g of spiro-(3,1-benzoxazine-6-nitro-4(2H)4'-piperidin)-2-one as the hydrochloride—m.p. 300° after recrystallization from water.

Step four: The title compound

Starting from a mixture of 4.32 g of spiro-(3,1-benzoxazine-6-nitro-4(2H)4'-piperidin)-2-one hydrochloride, 2.6 ml of triethylamine, 2.78 of potassium iodide, 4.3 g of anhydrous potassium carbonate, 3.73 g of 2-(3-chloropropyl)-2-(4-fluorophenyl)-5,5-dimethyl-1,3-dioxane in 60 ml di dimethylformamide, according to the previously reported procedure (see Example 1, step seven) 2.58 g of 1'-[3-(4-fluorobenzoyl)propyl]spiro(3,1-benzoxazine-6-nitro-4(2H)4'-piperidin)-2-one, m.p. 215°–216° are obtained.

EXAMPLE 4

1'-[3-(4-Fluorobenzoyl)propyl]spiro-(3,1-benzoxazine-6-fluoro-4(2H)4'-piperidin)-2-one

Step one: The intermediate 1'-methylspiro-(3,1-benzoxazine-6-amino-4(2H)4'-piperidin)-2-one A solution of 9.5 g of 1'-methylspiro-(3,1-benzoxazine-6-nitro-4(2H)4'-piperidin)-2-one (see Example 3) in 250 ml of absolute ethanol in hydrogenated over 3.8 g of 10% Pd/C. When no more hydrogen is absorbed the reaction mixture is filtered off and evaporated to dryness giving 7.75 g of 1'-methylspiro-(3.1-benzoxazine-6-amino-4(2H)4'-piperidin)-2-one, m.p. 247°–249° from ethanol.

Step two: The intermediate 1'-methylspiro-(3.1-benzoxazine-6-fluoro-4(2H)4'-piperidin)-2-one A solution of 3.9 g of sodium nitrite in 4.9 ml of water is added dropwise in 30 minutes to a stirred mixture of 12.2 g of the above prepared 6-amino derivative in 25.5 ml of water and 32 ml of a 40% aqueous solution of fluoboric acid at −5°.

After one hour the diazonium fluoborate precipatate is filtered off, dried under vacuum and then heated two hours at 190° under nitrogen. The resulting viscous residue is dissolved in water and extracted with ethyl acetate from the basified aqueous solution. By evaporation of the organic phase 7.38 g of 1'methylspiro-(3,1-benzoxazine-6-fluoro-4(2H)4'-piperidin)-2-one m.p. 221°–223°, are obtained.

Step three: The intermediate 1'cyanospiro-(3,1-benzoxazine-6-fluoro-4(2H)4'-piperidin)-2-one Starting from 7.5 g of the above prepared compound by treatment with 5.6 g of cyanogen bromide, according to the previously reported procedures, 7.6 g of 1'-cyanospiro-(3,1-benzoxazine-6-fluoro-4(2H)4'-piperidin)-2-one, m.p. 227°–229°, are obtained.

Step four: The intermediate spiro-(3,1-benzoxazine-6-fluoro-4(2H)4'-piperidin)-2-one Starting from 6.25 g of the above 1'-cyanospiro derivative, according to the previously reported procedure (see Example 1—step six), 5.5 g of spiro-(3,1-benzoxazine-6-fluoro-4'(2H)4'-piperidin)-2-one, m.p. 245°–247° are obtained.

Step five: The title compound

Starting from 4.8 g of spiro-(3,1-benzoxazine-6-fluoro-4(2H)4'-piperidin)-2-one, 3.46 g of potassium iodide, 5.8 g of anhydrous potassium carbonate, 5 g of 2-(3-chloropropyl)-2-(4-fluorophenyl)-5,5-dimethyl-1,3-dioxane in 55 ml of dimethylformamide, according to the previously reported procedure (see Example 1—step seven), 4.8 g of 1'-[3-(4-fluorobenzoyl propyl]spiro-(3,1-benzoxazine-6-fluoro-4(2H)4'-piperidin)-2-one, m.p. 170°–172° from ethyl acetate, are obtained.

EXAMPLE 5

1'-[3-(4-Fluorobenzoyl)propyl]spiro-(3,1-benzoxazine-6-cyano-4(2H)4'-piperidin)-2-one

Step one: The intermediate 1'-methylspiro-(3,1-benzoxazine-6-cyano-4(2H)4'-piperidin)-2-one A solution of 2 g of sodium nitrite in 5 ml of water is added dropwise to a mixture of 8.3 g of 1'-methylspiro-(3,1-benzoxazine-6-amino-4(2H)4'-piperidin)-2-one in 9.7 ml of water and 9.7 ml of concentrated hydrochloric acid at 0°. After one hour this cold solution containing the diazonium salt is added to a solution of 3.3 g of copper cyanide and 4 g of sodium cyanide in 10 ml of water warmed at 70°. After stirring one hour at this temperature and twenty minutes at 100° the mixture is cooled, basified and extracted with n-butanol. By evaporation under vacuum there are obtained 6 g of 1'- methylspiro-(3,1-benzoxazine-6-cyano-4(2H)4′-piperidin)-2-one m.p. 247°–249°.

Step two: The intermediate 1′-cyanospiro-(3,1-benzoxazine-6-cyano-4(2H)4′-piperidin-2-one Starting from 1.6 g of the above prepared compound and 1.5 g of cyanogenbromide, according to the previously reported procedure, 1.3 g of 1′-cyanospiro-(3,1-benzoxazine-6-cyano-4(2H)4′-piperidin)-2-one are obtained, m.p. 284°–286°.

Step three: The intermediate spiro-(3,1-benzoxazine-6-cyano-4(2H)4′-piperidin)-2-one A mixture of 2.7 g of the above prepared compound, 14 g of zinc dust in 250 ml of a 95% aqueous solution of acetic acid is heated at 80° for two hours. The solvent is evaporated and the residue is taken up with a mixture of chloroform and a 2N solution of ammonium hydroxide. Evaporation of the organic layer gives 1.3 g of spiro-(3,1-benzoxazine-6-cyano4-(2H)4′-piperidin)-2-one, m.p. 268°–270° from acetonitrile.

Step four: The title compound

Starting from 1 g of spiro-(3,1-benzoxazine-6-cyano-4(2H)4′-piperidin)-2-one, 0.73 g of potassium iodide, 1.23 g of anhydrous potassium carbonate and 0.99 g of 2-(3-chloropropyl)2-(4-fluorophenyl)-5,5-dimethyl-1,3-dioxane in 15 ml of dimethylformamide, according to the previously reported procedure (see Example 1—step seven) 0.6 g of 1′-[3-(4-fluorobenzoyl)-propyl]spiro-(3,1-benzoxazine-6-cyano-4(2H)4′-piperidin)-2-one m.p. 194°–195° from ethyl acetate are obtained.

EXAMPLE 6

1′-[3-(4-fluorobenzoyl)propyl]spiro-[3,1-benzoxazine-6-bromo-4(2H)4′-piperidin]-2-one, hydrochloride To a solution of 0,5 g of the compound prepared in Example 1, in 10 ml of ethanol, an excess of 5% hydrogen chloride in ethanol is added. Diethyl ether is added until complete precipitation.

The formed solid is filtered, washed with ether and recrystallized from i-propylalcohol.

0,48 g of the title compound are obtained, m.p. 248°–249°.

EXAMPLE 7

Preparation of tablets weighting 500 mg and containing 100 mg of active ingredient

| Ingredient | Quantity per 10000 tablets |
|---|---|
| 1′-[3(4-fluorobenzoyl)propyl]spiro-[3,1 benzoxazine-6-bromo-4(2H)—4′piperidin]-2-one | 1000 g |
| Mannitol | 3000 g |
| Sucrose 6 × | 500 g |
| Corn Starch | 300 g |
| Talc | 125 g |
| Magnesium stearate | 75 g |

All the ingredients except the corn starch, magnesium, stearate and talc are mixed, slugged and screened through a 20 mesh screen twice. The mixture so obtained is transferred to a twin-shell blender and, after addition of the corn starch, magnesium stearate and talc, mixed for 10 min. and compressed to weight using ½ in. flat-face bevel-edge punches.

We claim:

1. A compound of the formula 1′-[3-(4-fluorobenzoyl)-propyl]spiro-(3,1-benzoxazine-6-bromo-4(2H)4′-piperidin)-2-one, or a pharmaceutically-acceptable salt thereof.

2. A pharmaceutical composition for treating psychotic disorders in humans comprising:
    (a) an antipsychotic effective amount of the compound of claim 1; and
    (b) a pharmaceutically acceptable excipient.

3. A method for treating psychotic disorders in humans comprising administering to a subject in need of such treatment an antipsychotic effective amount of the compound of claim 1.

* * * * *